United States Patent [19]

Käbisch et al.

[11] 4,308,408

[45] Dec. 29, 1981

[54] PROCESS FOR THE HYDROXYLATION OF STYRENE AND STYRENE DERIVATIVES

[75] Inventors: Gerhard Käbisch; Horst Malitius; Siegfried Raupach; Rudolf Trübe; Hans Wittmann, all of Rheinfelden, Fed. Rep. of Germany

[73] Assignee: Degussa Aktiengesellschaft, Frankfurt, Fed. Rep. of Germany

[21] Appl. No.: 187,945

[22] Filed: Sep. 16, 1980

[30] Foreign Application Priority Data

Sep. 19, 1979 [DE] Fed. Rep. of Germany ....... 2937768

[51] Int. Cl.³ ............................................. C07C 33/26
[52] U.S. Cl. .................................... 568/811; 568/815
[58] Field of Search ................................ 568/811, 815

[56] References Cited

U.S. PATENT DOCUMENTS 2,437,648  3/1948  Milas .................................. 568/811
2,500,599  3/1950  Bergsteinson et al. ............. 568/811
3,337,635  8/1967  Norton et al. ....................... 568/811
3,373,206  3/1968  Rocca .................................. 568/811

*Primary Examiner*—Werren B. Lone
*Attorney, Agent, or Firm*—Cushman, Darby & Cushman

[57] ABSTRACT

Styrene or styrene substituted in the aromatic nucleus or on the vinyl group with a methyl group or styrene having the vinyl group substituted by hydroxymethyl is reacted with less than 2 moles of formic acid and less than 2 moles of hydrogen peroxide per mole of styrene or substituted styrene to hydroxylate the double bond. The formic acid is employed at a concentration between 20 and 100 weight percent and the hydrogen peroxide is employed at a concentration of less than 50 weight %. The concentration of the hydrogen peroxide in the aqueous phase of the reaction mixture is held below 15 weight percent during the entire reaction.

The corresponding diols or triols are formed directly from the olefins employed within reasonable reaction times in high yields.

24 Claims, No Drawings

PROCESS FOR THE HYDROXYLATION OF STYRENE AND STYRENE DERIVATIVES

SUMMARY OF THE INVENTION

The invention is directed to a process for the hydroxylation of styrene or styrene which is substituted in the aromatic nucleus or on the vinyl group by a methyl group or which is substituted on the vinyl group by a hydroxymethyl group. Such compounds by the formula

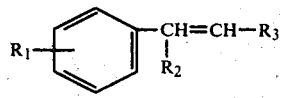

where $R_1$ is hydrogen or methyl, $R_2$ is hydrogen or methyl and $R_3$ is hydrogen or hydroxymetyl with the proviso that not over one of $R_1$, $R_2$ and $R_3$ is other than hydrogen.

Under "hydroxylation" is meant that across the vinyl double bond or substituted vinyl double bond there are placed two hydroxyl groups, thus a vicinal diol is formed.

The process of the invention is carried out by reacting the olefin to form the hydroxylated derivatives at a temperature between 40° and 80° C. with less than 2 moles of formic acid, e.g., as little as 0.1 mole, and less than 2 moles of hydrogen peroxide, e.g., as little as 1.0 mole, in each case per mole of double bond to be hydroxylated. Formic acid is employed with a concentration between 20 and 100 weight percent and hydrogen peroxide with a concentration of less than 50 weight percent and the concentration of the hydrogen peroxide in the aqueous phase of the reaction mixture during the entire duration of the reaction is held below 15 weight percent.

Preferably the reaction is undertaken at a temperature between 45° and 60° C. The formic acid is employed advantageously in an amount of 0.2 to 0.8 mole per mole of double bond to be hydroxylated, the hydrogen peroxide is employed advantageously in an amount of 1.1 to 1.5 moles per mole of double bond to by hydroxylated.

Preferably there is used hydrogen peroxide with a concentration of 15 to 40 weight percent.

For example through the process of the invention there can be changed styrene into phenyl glycol, the various vinyl toluenes (i.e., ortho, meta and para toluene into the corresponding tolyl glycols, α-methyl styrene into α-methyl phenyl glycol or cinnamyl alcohol into phenyl glycerine. The reaction proceeds surprisingly very smoothly despite the relatively mild reaction conditions and within a reasonable reaction time leads to high yields of the desired vicinal diols.

In the practical carrying out of the process of the invention, preferably the entire amount of formic acid is present initially. Also the entire amount of hydrogen peroxide to be employed can be present. In these cases then the olefin to be hydroxylated is slowly metered in. However, it is normally more suitable to have present together with the total amount of formic acid and the hydrogen peroxide about one-third of the total amount of olefin to be hydroxylated and to slowly meter in the remainder of the olefin to be hydroxylated. In every case the reaction mixture is stirred intensely. To improve the conversion there is recommended an appropriate post reaction time after all the reactants are combined in the reaction vessel.

After the end of the reaction the vicinal diols formed are usually present dissolved in the aqueous phase. This type of aqueous solution can be used directly for many purposes. In most cases, however, not only does the residual hydrogen peroxide cause disturbances but it is also desired that the vicinal diols be isolated in pure form. For the working up then various modes of action can be considered.

In case the olefin is not completely reacted, or to a small extend polymerized during the reaction, so that a second phase separates, there is first carried out a phase separation. Alternatively, the non-reacted olefin can be distilled off.

In many cases it is then advisable to substantially decompose the hydrogen peroxide still contained in the aqueous phase. The decomposition can be effected by prolonged standing at higher temperatures (digestion) or by the action of a suitable catalyst (e.g., leading over a platinum fixed bed-catalyst) or by a combination of these two procedures.

Then suitably the reaction mixture, in a given case after neutralization of the formic acid, is concentrated by distilling off the water. In case the formic acid present is neutralized, an extraction with a suitable solvent, for example, ethyl acetate follows. The solvent is distilled off from the extract and the remaining residue of crude diol, in a given case through heating under reduced pressure, freed from any water still present. Alternatively, there can be eliminated the neutralization of the formic acid contained in the reaction mixture. Then it is suitabled either to continuously carry out the concentration according to a type of steam distillation and to continue until the distillate only contains small amounts of formic acid. Or the stripping of the formic acid is carried out discontinuously in a way that the residue after stripping the main amount of formic acid is treated again with water, concentrated again and this operation repeated several times. The remaining residue of crude diol can then be freed again from volatile components still contained through heating under reduced pressure.

The thus obtained crude diols are present with a degree of purity of about 88 to 96%. Insofar as a still further purification is necessary, this can be effected in customary manner by recrystallization or by fractionated distillation under reduced pressure.

Unless otherwise indicated all parts and percentages are by weight.

The process of the invention can comprise, consist essentially of or consist of the steps set forth with the recited materials.

The process of the invention is explained in more detail in the following examples.

DETAILED DESCRIPTION

EXAMPLE 1

In a 2 liter multiple necked flask equipped with a stirrer, reflux condenser, dropping funnel and thermometer which is thermostatically adjusted to 50° C. are intensively mixed 590 grams (2.6 moles) of aqueous hydrogen peroxide (15%) and 141 grams (3.0 moles) of formic acid (98%).

To this mixture there was metered in 208 grams (2.0 moles) of styrene (stabilized with 0.5 gram of hydroquinone, specifically the first 70 grams within 10 minutes and the remainder in the course of 4 hours). After a total time of 10 hours, the reaction mixture was next cooled and freed from 8 grams of styrene (and polystyrene) by filtration. Accordingly, the reaction amounted to 96.2%. Next the reaction mixture was subjected to a steam distillation at normal pressure until the formic acid concentration in the aqueous distillate had fallen from an initial 7.8% to 0.8%. By heating under reduced pressure, the residual portions of water and formic acid were removed. There remained a residue of 271 grams having a phenyl glycol content of 89.5%.

EXAMPLE 2

In a stirred apparatus according to Example 1 there were present 104 grams (1.0 mole) of styrene (stabilized with 0.5 gram of 2,6-di-tert.-butyl-4-methyl-phenol) and
141 grams (3.0 moles) of formic acid (98%).

In the course of one hour at 50° C., there were metered into this stirred mixture 255 grams (1.5 moles) of aqueous hydrogen peroxide (20%). Subsequently stirring was continued for a further hour to 50° C. Then in the course of a further 4 hours there were simultaneously metered in at 55° C.

208 grams (2.0 moles) of styrene (stabilized as above) and 595 (3.5 moles) of aqueous hydrogen peroxide (20%) and stirring carried out for a further 4 hours.

There were distilled off 25 grams of styrene from the reaction mixture. The reaction accordingly amounted to about 92%. The reaction mixture was adjusted to neutral with 300 grams of aqueous sodium hydroxide (40%) and concentrated somewhat by topping off 300 ml of water. The now two-phased mixture was freed of hydrogen peroxide residue by leading it over a fixed bed catalyst (0.1% platinum on Berl saddles) and extracted five times in succession, each time with 200 ml of ethyl acetate. In the concentration of the combined ethyl acetate extracts there remained behind 342 grams of residue which corresponds to a phenyl glycol crude yield of 90%. By recrystallization or total distillation under reduced pressure the crude phenyl glycol can be easily converted into a pure product with a melting point of 66°-67° C.

EXAMPLE 3

Example 2 was repeated with the difference that in place of a total of 312 grams (3.0 moles) of styrene there were employed 354 grams (3.0 moles) of vinyl toluene (commercial mixture of meta and para isomers).

After the end of the reaction there were recovered 28 grams of vinyl toluene. Accordingly, the reaction amounted to about 92%.

With the concentration of the ethyl acetate extracts there were obtained 411 grams of crude tolyl glycol, which corresponds to a yield of 98%. By distillation at 0.1 Torr there were obtained 318 grams of pure diol (boiling point 123°-126° C.).

EXAMPLE 4

There were present in a stirred apparatus according to Example 1

118 grams (1.0 mole) of α-methyl styrene (2-phenyl propene) and
141 grams (3.0 moles) of formic acid (98%).

There were metered into this stirred mixture in the course of 5 hours 236 grams (2.0 moles) of α-methyl styrene and
850 grams (5.0 moles) of aqueous hydrogen peroxide (20%).

After a post reaction time of a further 2 hours there were distilled off from the reaction mixture 17 grams of α-methyl styrene. Accordingly, the reaction amounted to 95%. The reaction mixture was neutralized with 285 grams of aqueous sodium hydroxide (40%) and concentrated by topping of 300 ml of water. There remained behind a mixture which separated into two phases. The organic phase was separated off and washed in portions with the previously topped off water.

The wash waters were combined with the aqueous phase, catalytically freed from residual hydrogen peroxide and extracted five times in succession, in each case with 200 ml of ethyl acetate. By concentration of the combined ethyl acetate extracts there were obtained 70 grams of diol with a degree of purity of 96%.

The separated organic phase was subjected to a total distillation under reduced pressure. Thereby there were obtained the following fractions:

Fraction 1: 90 grams of water
Fraction 2: 73 grams (identified as acetophenone)
Fraction 3: 247 grams of diol (9%; boiling point at 0.1 Torr 104°-106° C.)
Residue: 38 grams (unidentified)

Accordingly, altogether there were obtained of 2-phenyl propanediol-1,2

247 grams with a purity of 99% = 245 grams (100%)
70 grams with a purity of 96% = 67 grams (100%)
together 312 grams (100%) which corresponds to a yield of 72%.

The entire disclosure of German priority application No. P 29 37 768.2-42 is hereby incorporated by reference.

What is claimed is:

1. A process of forming a vicinal diol from styrene or styrene substituted in the aromatic nucleus or on the vinyl group with a methyl group or substituted on the vinyl group with a hydroxymethyl group comprising hydroxylating said styrene or substituted styrene to form the corresponding vicinal diol at a temperature between 40° and 80° C. with formic acid and aqueous hydrogen peroxide, the formic acid and hydrogen peroxide each being used in an amount of less than 2 moles per mole of double bond being hydroxylated, the formic acid being added in a concentration between 20 and 100 weight percent, the hydrogen peroxide being added in a concentration less than 50 weight percent and the concentration of the hydrogen peroxide in the aqueous phase of the reaction mixture during the entire time of the reaction being held below 15 weight percent.

2. The process of claim 1 wherein the compound being hydroxylated is styrene, ring substituted methyl styrene, α-methyl styrene or cinnamyl alcohol.

3. The process of claim 2 wherein the compound being hydroxylated is styrene, meta methyl styrene, para methyl styrene or α-methyl styrene.

4. The process of claim 3 wherein the compound being hydroxylated is styrene.

5. The process of claim 3 wherein the compound being hydroxylated is mixed meta-para styrene.

6. The process of claim 2 wherein the reaction is carried out at a temperature between 45° and 60° C.

7. The process of claim 6 wherein the formic acid is added in an amount of 0.2 to 0.8 mole per mole of double bond being hydroxylated.

8. The process of claim 2 wherein the formic acid is added in an amount of 0.2 to 0.8 mole per mole of double bond being hydroxylated.

9. The process of claim 7 wherein the hydrogen peroxide is added in an amount of 1.1 to 1.5 moles per mole of double bond being hydroxylated.

10. The process of claim 6 wherein the hydrogen peroxide is added in an amount of 1.1 to 1.5 moles per mole of double bond being hydroxylated 11. The process of claim 2 wherein the hydrogen peroxide is added in an amount of 1.1 to 1.5 moles per mole of double bond being hydroxylated.

12. The process of claim 8 wherein the hydrogen peroxide is added in an amount of 1.1 to 1.5 moles per mole of double bond being hydroxylated.

13. The process of claim 12 wherein the hydrogen peroxide is added in a concentration of 15 to 40 weight percent.

14. The process of claim 11 wherein the hydrogen peroxide is added in a concentration of 15 to 40 weight percent.

15. The process of claim 10 wherein the hydrogen peroxide is added in a concentration of 15 to 40 weight percent.

16. The process of claim 9 wherein the hydrogen peroxide is added in a concentration of 15 to 40 weight percent.

17. The process of claim 7 wherein the hydrogen peroxide is added in a concentration of 15 to 40 weight percent.

18. The process of claim 6 wherein the hydrogen peroxide is added in a concentration of 15 to 40 weight percent.

19. The process of claim 2 wherein the hydrogen peroxide is added in a concentration of 15 to 40 weight percent.

20. The process of claim 2 wherein the formic acid is added in an amount not over 0.8 mole per mole of double bond being hydroxylated.

21. The process of claim 20 wherein the hydrogen peroxide is added in an amount not over 1.5 moles per mole of double bond being hydroxylated.

22. The process of claim 2 wherein the hydrogen peroxide is added in an amount not over 1.5 moles per mole of double bond being hydroxylated.

23. The process of claim 1 wherein the reaction time is up to 10 hours.

24. The process of claim 23 wherein the reaction is 7 to 10 hours.

* * * * *